Figure 1:
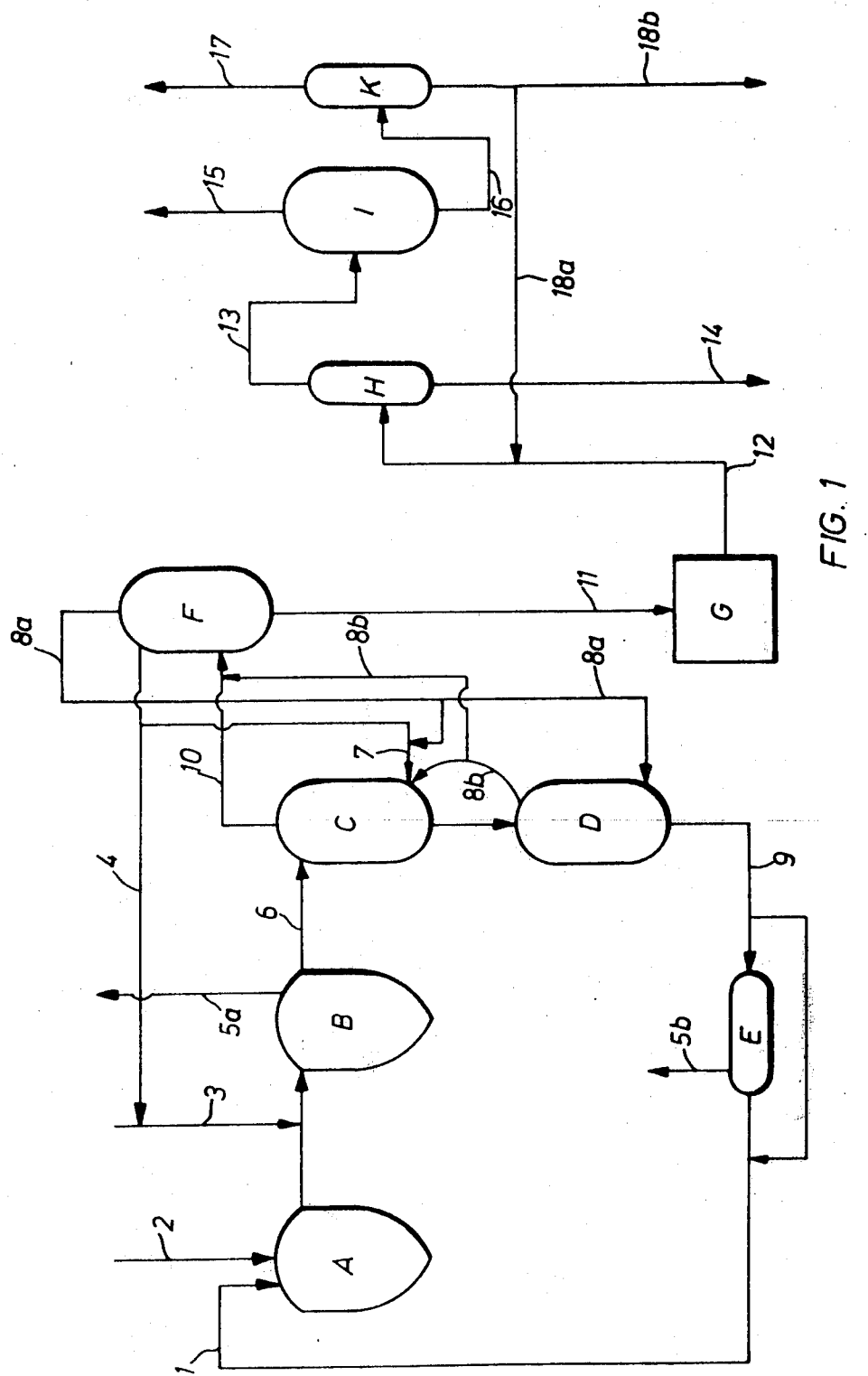

United States Patent [19]
Knöfel

[11] 3,952,042

[45] Apr. 20, 1976

[54] PROCESS FOR THE PRODUCTION OF POLYISOCYANATES

[75] Inventor: Hartmut Knöfel, Leverkusen, Germany

[73] Assignee: Bayer Aktiengesellschaft, Leverkusen, Germany

[22] Filed: Nov. 11, 1974

[21] Appl. No.: 522,618

[30] Foreign Application Priority Data
Nov. 14, 1973  Germany............................ 2356828

[52] U.S. Cl........................ 260/453 PH; 260/570 D
[51] Int. Cl.².............. C07C 118/02; C07C 119/048
[58] Field of Search... 260/453 AM, 570 D, 453 PH

[56] References Cited
UNITED STATES PATENTS 3,012,008  12/1961  Lister.............................. 260/453 X
3,367,969  2/1968  Perkins............................... 260/570

*Primary Examiner*—Elbert L. Roberts
*Assistant Examiner*—Dolph H. Torrence
*Attorney, Agent, or Firm*—Joseph C. Gil; Gene Harsh

[57] ABSTRACT

A process is provided for making a mixture of diisocyanate and polyisocyanates having more than two amino groups of the diphenylmethane series which has a low content of the o-isomers wherein a mixture of aniline and a polyamine prepared by condensation of aniline and formaldehyde is condensed with formaldehyde, at least 90% of the amino groups in the mixture being protonized with an acid, and phosgenating the resulting condensation product to form corresponding polyisocyanates.

2 Claims, 2 Drawing Figures

PROCESS FOR THE PRODUCTION OF POLYISOCYANATES

This invention relates generally to organic polyisocyanates, and more particularly, to a process for making mixtures of diisocyanates and higher functional polyisocyanates of the diphenylmethane series which have a low o-isomer content.

It is known that pure 4,4'-diisocyanato-diphenylmethane and mixtures of polyisocyanates of the diphenylmethane series may be prepared by phosgenating polyamine mixtures of the kind which are obtained by condensing aniline with formaldehyde in acid solution. The catalyst used for preparing the polyamine mixtures is preferably hydrochloric acid. In addition to containing 4,4'-diaminodiphenylmethane, these polyamine mixtures contain isomeric diamines and higher molecular weight polyamines as well as minor quantities of N-substituted by-products (German Offenlegungsschrift No. 1,913,473; 1,937,685 and 2,032,336).

Polyamine mixtures which contain a high proportion of 4,4'-diaminodiphenylmethane are obtained if condensation is carried out with a molar ratio of aniline to hydrogenchloride close to 1 and a large excess of aniline and low initial temperatures are employed (U.S. Pat. No. 2,818,433 and German Offenlegungsschrift No. 1,442,459; 1,959,168 and 2,134,756). The addition of excess aniline after termination of the primary reaction of aniline with formaldehyde is advantageous for the diamine yields obtained in the polyamine mixture (U.S. Pat. No. 3,367,969).

This procedure also suppresses the formation of unwanted by-products but, even when the process is carried out in this way, the polyisocyanate mixtures obtained generally contain not less than 3% of 2,4'-diisocyanato-diphenylmethane. To obtain pure 4,4'-diisocyanato-diphenylmethane it is, therefore, necessary to subject the polyisocyanate mixture to fractional distillation or crystallization.

In principle, it may be said that the 2,4'-diaminodiphenylmethane content in the polyamine mixture can most suitably be controlled by the molar ratio of aniline to acid employed, a low aniline/acid ratio resulting in a high proportion of 2,4'-diamino-diphenylmethane. The proportion of higher nuclear products in the polyamine mixture is on the other hand, determined mainly by the molar ratio of aniline to formaldehyde, the proportion of higher nuclear polyamines in the condensation product increasing with decreasing aniline/formaldehyde ratio. The known processes for producing polyisocyanates of the diphenylmethane series which have a low o-isomer content and the known processes for producing pure 4,4'-diisocyanato-diphenylmethane therefore have the following main disadvantages:

1. the large quantities of hydrochloric acid used as catalyst must be removed by expensive neutralization methods and cause serious environmental problems (contamination of effluent water) and/or
2. the polyisocyanate mixture obtained by phosgenation of the resulting polyamine mixture must be processed by elaborate distillation or crystallization methods.

It is, therefore, an object of this invention to provide a process for making a mixture of diisocyanates and higher functional polyisocyanates having a low o-isomer content which is devoid of the foregoing disadvantages. A more specific object of the invention is to provide a process for making mixtures of diisocyanate and higher functional polyisocyanates having a low 2,4'-diphenylmethane diisocyanate content which does not require large quantities of acid catalyst and elaborate distillation for separation of 4,4'-diphenylmethane diisocyanate from the 2,4'-isomer. Still another object of the invention is to provide a new process for the production of polyisocyanates of the diphenylmethane series by which polyisocyanates of the diphenylmethane series with a low o-isomer content and pure 4,4'-diisocyanato-diphenylmethane may be prepared, in which process the above mentioned problems of neutralization and contamination of the effluent water are virtually eliminated and 4,4'-diisocyanato-diphenylmethane can be obtained in maximum yields with minimum distillation effort.

Figure 2:
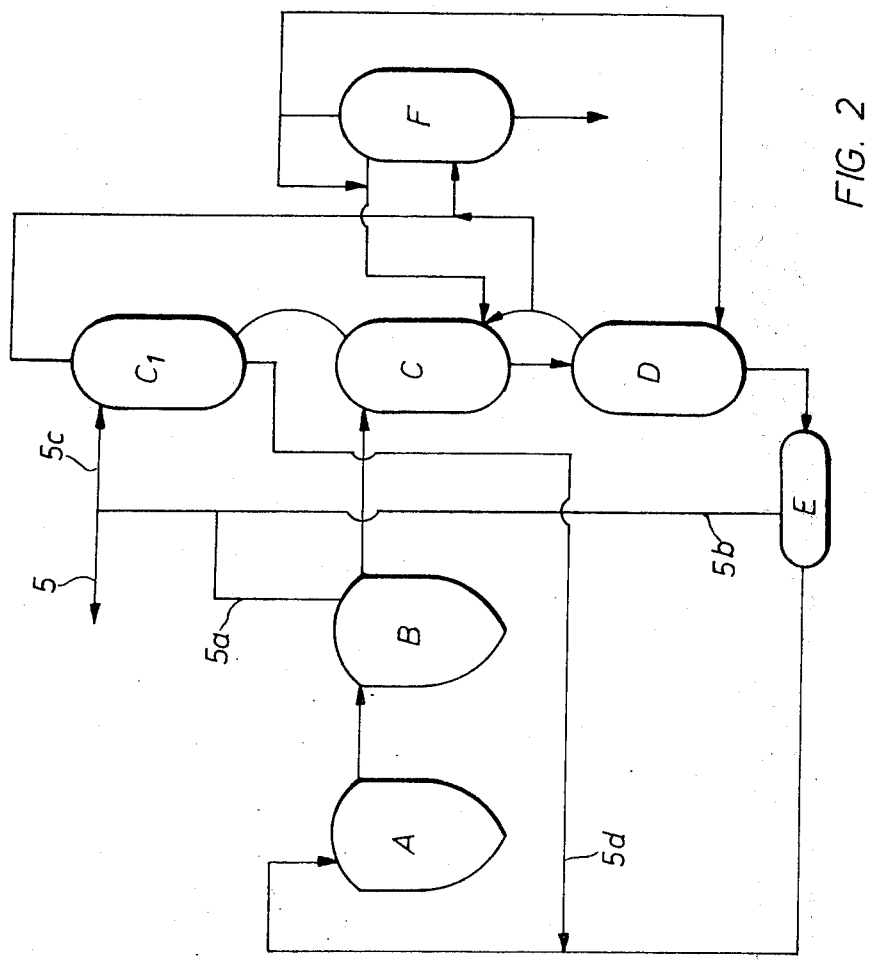

Other objects will become apparent from the following description with reference to the accompanying drawing wherein FIG. 1 is a diagramatic illustration of one embodiment of the invention; and FIG. 2 illustrates diagramatically another embodiment of the invention.

The foregoing objects and others are accomplished in accordance with this invention, generally speaking, by providing a process for the simultaneous production of diisocyanates and higher functional polyisocyantes of the diphenylmethane series by reacting an at least partly protonated arylamine with formaldehyde in the aqueous phase, separating the aniline/formaldehyde condensate from the resulting reaction product, phosgenating the separated aniline/formaldehyde condensate and working up the resulting polyisocyanate mixture by distillation, which process is characterized in that 1. The at least partly protonated arylamine used is a mixture of
    a. aniline and
    b. a polyamine of the diphenylmethane series obtained by aniline/formaldehyde condensation, in which mixture
   the proportion of (a) to (b) corresponds to a ratio of aniline amino groups to polyamine amino groups of between 98:20 and 20:80 and at least 90% of the amino groups in the mixture are protonated,
2. the molar ratio of aniline to formladehyde at the beginning of the reaction is between 1:1 and 12:1,
3. the condensation reaction is carried out in at least two stages, the reaction temperature in the first stage being 20° to 60°C and the reaction temperature in the last condensation stage being above 60°C,
4. the separation of the polyamine which is required to be phosgenated is carried out by
    a. extraction in at least two stages of the reaction mixture formed in the reaction by means of a hydrophobic solvent in the presence of additional aniline which is added to the condensation product in the aqueous phase either during and/or after the condensation reaction, and
    b. removal of water, hydrophobic solvent and aniline by distillation from the resulting organic phase, preferably after any minor quantities of acid present in the form of ammonium salts have been washed out with water and/or neutralized with an aqueous inorganic base,
    a a. the extraction being carried out at temperatures above 60°C in all stages of the extraction process, a b. the mixture which is supplied to the first extraction stage for extraction containing 10 to 60 percent by weight of free arylamine, a c. the hydrophobic solvent supplied to the first extraction stage containing 10 to 80 percent by weight of free aniline, a d. the hydrophobic solvent supplied to the last extraction stage containing a maximum of 10 percent by weight of free aniline; and 5. the aqueous phase resulting from the extraction process being returned to the beginning of the process.

The process according to the invention is thus a two-stage process wherein 1. a polyamine mixture is prepared; and
2. this polyamine mixture is phosgenated to the corresponding polyisocyanate mixture and is distilled.

The starting material used for the process according to the invention is an aqueous solution of arylamines in which at least 90 percent of the amino groups content is protonated. The arylamines are mainly a mixture of aniline and polyamines of the diphenylmethane series of the kind which can be obtained by aniline/formaldehyde condensation. The proportions of aniline to polyamine used correspond to a molar ratio of aniline to amino groups in the polyamines of between 98:2 and 20:80, preferably 90:10 and 40:60. At least 90 percent of the arylamine is in the protonated form. This means that at least 90 percent of the amino groups in the mixture have been converted into ammonium groups by reaction with an acid. Acids suitable for this purpose are, for example, water-soluble acids with pKa-values below 2.5 and preferably below 1.5, for example hydrochloric, hydrobromic, sulphuric, trifluoroacetic, methane sulphonic, trifluoromethane sulphonic or benzene sulphonic acid. Hydrochloric acid is preferably used.

The proportion by weight of water to arylamine in the aqueous solution is preferably from 0.2:1 to 3:1.

Before the process according to the invention is carried out, the aqueous arylamine solution is mixed with formaldehyde, compounds which split off formaldehyde or compounds which react like formaldehyde, preferably with aqueous formalin solution, in proportions such that the molar ratio of aniline to formaldehyde in the reaction mixture is from 1:1 to 12:1, preferably from 3:1 to 8:1.

The resulting reaction mixture is then subjected to a condensation reaction known per se which is carried out in at least two stages, precondensation being carried out at 20° to 60°C in the first stage while the last stage is carried out at temperatures above 60°C and preferably 80° to 110°C, most preferably 90°–100°C. The condensation reaction may take place in two or more stages in known manner. When an aniline to formaldehyde ratio of less than 3:1 is used at the beginning of the reaction it is advisable to add a fresh portion of aniline after the first condensation stage.

The aqueous reaction mixture from the last condensation stage is then supplied to the extraction process which is carried out in at least two stages as follows:

In the first, major, extraction stage, the aqueous phase to which an additional quantity of aniline has been added before the last condensation stage and/or before the first extraction stage is extracted with aniline-containing hydrophobic solvents for the polyamines to remove a quantity of polyamines of the diphenylmethane series corresponding substantially to the quantity of formaldehyde added at the beginning of the process.

In the second extraction stage excess free amine is removed from the aqueous phase by extraction with hydrophobic solvent therefor which may already contain aniline but its aniline content is lower than that of the solvent used in the first stage, i.e. it is generally below 10 percent. The aqueous solution leaving the second extraction stage is therefore substantially similar in composition to the aqueous arylamine solution used at the beginning of the process, apart from possibly having a higher water content.

This aqueous amine solution is then returned to the beginning of the process, optionally after removal of some of its water by distillation.

The hydrophobic solvents used for the process according to the invention may be any solvents for the amines and polyamines which are immiscible with water and inert towards the reaction components and which have boiling points approximately in the region of 60° to 250°C and preferably 80° to 200°C and the density of which is sufficiently different from the density of water to insure efficient phase separation. Particularly suitable organic solvents are chlorobenzene, dichlorobenzenes, benzene, toluene, the xylenes, dichloroethane, chloroform, carbon tetrachloride and the like. Commercial xylene or o-xylene are preferred.

Before the aqueous system which is required to be extracted enters the first extraction stage, it contains 10 to 60 and preferably 12 to 30 percent by weight of free arylamine, i.e. arylamine which is not protonated. This free, unprotonated arylamine content is adjusted by the addition of aniline to the aqueous solution before the last condensation stage and/or immediately before the first extraction stage.

The hydrophobic solvent used in the first extraction stage has a free aniline content of 10 to 80 percent by weight.

The concentration of free amines in the aqueous phase and organic phase is preferably adjusted so that the solution pressure of free arylamine in the aqueous phase on entering the extraction stage is equal to or greater than the solution pressure of arylamine in the organic phase at the same point of the extraction stage. This concentration of acid, in the aqueous phase with free aniline not bound by salt formation relieves the load on the extraction apparatus in that the exchange of aniline from the organic phase for polyamine from the aqueous phase can take place right from the beginning and no additional volume is required for exchange to adjust the equilibrium of free amine in the aqueous and/or organic phase.

The organic phase leaving the first extraction stage is separated by distillation into solvent, aniline and aniline/formaldehyde condensate.

The aqueous solution leaving the first extraction stage is freed substantially from excess free amine in the second extraction stage by means of a hydrophobic solvent which has a maximum aniline content of 10 percent by weight, as already described above. The organic solution leaving the second extraction stage may be partly or completely used again as organic solution for the first extraction stage, if necessary after further addition of aniline. Alternately, however, the streams of solvent from the first and second extraction stage may, of course, be completely separated, i.e. the organic solution leaving the second extraction stage which contains aniline and aniline/formaldehyde condensates, may be treated directly by distillation.

The proportion by volume of aqueous solution to aniline-containing solvent in the first extraction stage may vary within relatively wide limits and is generally between 0.2:1 and 5:1.

The temperature in both the first and the second extraction stage is generally above 60°C and preferably between 90° and 120°C.

An important feature of the process according to the invention lies in the return of the aqueous protonized amine solution from the extraction stage to the reaction, which aqueous protonized amine solution may contain considerable quantities of polyamine in addition to aniline. Expressed in amine equivalents this means that, as already mentioned above, the proportion of aniline to polyamine in the aqueous solution leaving the last stage of extraction and returned to the beginning of the process may be between 98:2 and 20:80 and is preferably between 90:10 and 40:60. It was, from the start, not to be expected that this proportion of polyamines would only insignificantly reduce the yield of diamine, based on the amount of aniline and formalin introduced. The explanation of this unexpected finding is believed to be that, under the reaction conditions, formaldehyde reacts preferentially with those phenyl groups which have an unsubstituted position para to the amino group and that the returned polyamine consists almost exclusively of components which do not have such a free para-position.

The water of reaction and the water introduced with the formalin solution must be removed from the cycle of aqueous protonized arylamine solution because it would otherwise alter the concentrations in the reaction mixture. This may advantageously be carried out by flash evaporation in a vacuum, preferably employing pressures of less than 150 Torr, either during the reaction before the extraction stage at a temperature above 60°C and/or when the arylamine hydrochloride solution is returned to the reaction after the extraction stage. If the last mentioned method is employed, the arylamine hydrochloride solution is cooled down at the same time, which is in any case necessary for carrying out the reaction at a temperature below 60°C.

The organic phase discharged from the extraction process, which contains hydrophobic solvent, aniline, polyamine mixture and a certain amount of water, may also contain minor quantities of protonized arylamine which have been carried along. The extracted product is therefore preferably alkalized in known manner before it is processed by distillation. The extracted product is advantageously washed with water before it is alkalized to reduce the load of acid. The wash-water used for this purpose may the condensate obtained from the process of evaporation under vacuum or some other water removed from the process, which may contain aniline.

The organic phase with hydrophobic solvent, aniline, polyamine mixture and small quantities of water remaining after the extracted product has been alkalized is worked up by distillation in the usual manner, purified hydrophobic solvent, aniline and polyamine mixture being obtained.

The extraction apparatus used for acid aqueous solutions containing aniline and polyamine and for free amines in a hydrophobic solvent must be made of corrosion-resistant material. For commercial scale apparatus, the use of glass, ceramics or materials containing mainly carbon may cause problems because of the high cost of construction and for reasons of safety owing to the sensitivity of the materials to impact or high tensile forces. It has been found that titanium and titanium/palladium alloys are resistant to the above-mentioned media at all the concentrations and temperatures which occur in practice and fulfill all the requirements for the construction of large-scale apparatus.

When the polyamine mixture is phosgenated by known methods in an inert solvent such as chlorobenzene it gives rise to a polyisocyanate mixture which can be treated in known manner and which may either be separated into a polyisocyanate mixture and a mixture which contains mostly diisocyanates or processed directly by fractional distillation.

Purification of the 4,4'-diisocyanato-diphenylmethane obtained is advantageously carried out by fractional distillation in at least two additional stages, using high vacuum trickle film columns. In the first stage, a distillate enriched in 2,4'-diisocyanato-diphenylmethane is separated from the sump product which has a reduced 2,4'-diisocyanate-diphenylmethane content and, in the second stage, 4,4'-diisocyanato-diphenylmethane is separated from a pump which contains polymer. The sump from the final distillation stage can be returned to the first distillation stage or it may be mixed with the polyisocyanate which remains after removal of the diisocyanates or the distillate which has been enriched with 2,4'-diisocyanato-diphenylmethane.

As already explained above, one of the major advantages of the process provided by the invention lies in the possibility of carrying out the aniline/formaldehyde condensation in the presence of quantities of acid which are almost equivalent to the amino groups and without the problems of salt accumulation and contamination of effluent water which are encountered in the known processes of the art. Because of the high degree of protonization of the amines used, condensation products which have only low o-isomer contents are preferentially formed. The process provided by the invention therefore particularly facilitates the preparation of 4,4'-diisocyanato-diphenylmethane in high yields and with less effort required for distillation than in the known processes of the art. The process according to the invention is suitable for preparing 4,4'-diisocyanato-diphenylmethane with a 2,4'-diisocyanato-diphenylmethane content of less than 3%. In principle, a 4,4'-diisocyanato-diphenylmethane which is almost free from isomer can be obtained by fractional distillation alone from polyisocyanate mixtures of the kind which can be prepared from aniline/formaldehyde condensates. This fractional distillation, however, is carried out under conditions at which part of the isocyanates is already lost by polymerization and mainly by carbodiimide formation. An economic process must have the aim of keeping down the amount of effort required for fractionation and hence improving the yield. The process according to the invention makes it possible for a phosgenation product to be prepared which, even before it is purified by distillation, already contains at least 85% by weight of 4,4'-diisocyanato-diphenylmethane.

In addition to making it possible for 4,4'-diisocyanato-diphenylmethane to be prepared in high yields, the process according to the invention also makes it possible for substantial proportions of higher nuclear polyisocyanates of the diphenylmethane series to be obtained with a reduced o-isomer content, the proportion obtained depending on the aniline/formaldehyde ratio selected at the beginning of the reaction. Another advantage of the process according to the invention is therefore to be seen in the fact that the yield of diisocyanates and of higher nuclear polyisocyanates can be varied within wide limits without requiring additional apparatus.

According to a special method of carrying out the multi-stage fractional distillation of the polyisocyanate mixture after separation of the diisocyanate isomer mixtures obtained, this separation process is carried out in two stages. In the first stage, isomeric 2,4'-diisocyanato-diphenylmethane is separated from the polymer formed and, in the second stage, 4,4'-diisocyanato-diphenylmethane is separated. A certain amount of 4,4'-diisocyanato-diphenylmethane is left dissolved in the polymer-containing sump in order that the sump have a lower viscosity and therefore be easier to handle. The valuable 4,4'-diisocyanato-diphenylmethane which contains very little of its isomer can be recovered from this sump solution by feeding it back to the distillation stage in which the diisocyanate is separated.

The carbodiimides contained in the polymer, which contain isocyanato-diphenylmethane groups as substituents, are, at the same time, subjected to an exchange reaction between isocyanate and carbodiimide. Higher molecular weight polyisocyanates displace the isocyanato-diphenylmethane groups on the carbodiimide bond and thus liberate diisocyanate. The yield of 4,4'-diisocyanato-diphenylmethane is thereby increased.

The method of carrying out the process according to the invention will now be explained with reference to FIGS. 1 and 2.

In FIG. 1:

A represents a reactor for carrying out the precondensation,

B represents a reactor for carrying out the final reaction,

C represents an extractor for carrying out the main extraction,

D represents an extractor for carrying out the final extraction,

E represents a vacuum vessel for distillation off water,

F represents a distillation apparatus for separating the organic phase,

G represents a phosgenation apparatus,

H represents a distillation apparatus for separating the diisocyanate from the polyisocyanate mixture, I represents a distillation apparatus for separating isomers and K represents a distillation apparatus for separating the polymer.

To carry out the process according to the invention, aqueous protonized arylamine solution 1 and formalin 2 are mixed in the container A by known methods. If desired, the mixing of these two components may also be carried out with the aid of the usual commercial mixing apparatus such as mixing nozzles, mixing pumps, reaction coils or static mixers. The container A may be a tank, reaction tower, reaction tube or the reaction coil mentioned above or a combination of several such pieces of apparatus. The heat liberated in the reaction may be removed by external cooling in heat exchangers or it may be removed directly from container A. In order to obtain high diamine yields, it is advisable to carry out the condensation in the first stage at a temperature below 40°C and preferably at 30° to 35°C. Temperatures above 40°C may be employed for preparing polyamine mixtures with lower diamine contents.

The second stage, which is accompanied by molecular rearrangement of the condensation products originally formed, may be carried out at a temperature above 60°C, preferably at 90° to 100°C, in another reaction chamber B. If the reaction is carried out at a pressure above 1 bar, it may also be carried out at temperatures above 100°C.

This reaction chamber may, like container A, consist of several pieces of apparatus connected together. The fresh aniline 3 and circulated aniline 4 may be fed in at any point but, in order to obtain high diamine yields, they are preferably introduced at a point before the final temperature is reached before the last condensation stage. It is also possible, for example, to add all the fresh aniline 3 required for the condensation reaction together with the circulated aniline 4 to the aqueous phase 6 immediately before its entry into the extractor C (not shown). Introduction of aniline into the reaction chamber B may also take place at several points. Water 5 $a$ may be removed from the reaction mixture in the reaction chamber B by distillation. The reaction mixture is then transferred from the reaction chamber B to an extraction stage C in which the polyamine is washed out with aniline 7 and solvent 8 $a$ and/or with aniline 7 and the solvent 8 $b$ from the following extraction stage D, which solvent is enriched in aniline. Since the reaction may also be completed at the extraction stage, the aniline 7 introduced into the extraction stage C also helps to increase the yield of diamine. To obtain high diamine yields, it is preferable to introduce a total of more than 10 mols of aniline into the reaction system for each mol of reacted formaldehyde.

In the extraction stage D, any arylamine not bound as a salt is washed out of the aqueous phase with hydrophobic solvent, preferably xylene. The quantity of free arylamine (not bound as salt) remaining in the aqueous phase 9 varies according to the quantity and composition of the solvent 8 $a$ which may contain varying quantities of aniline and on the efficiency of the extraction stage D.

The concentration of polyamine in the aqueous protonized arylamine solution 9 is determined by the quantitative proportions of the streams 6, 6, 8 $a$ and 8 $b$, by their composition and by their efficiency of the extraction stages C and possibly D. The aqueous solution 9 leaving the extractor D is returned to the beginning of the process, optionally first passing through the flash evaporator E for the purpose of partial removal of water 5 $b$ by distillation.

The apparatus used for extraction stages C and D may be any apparatus conventionally used for this purpose, e.g. mixers/separators, packed columns or columns with sieve shelves with or without pulsation or centrifuges.

The isolation of the organic phase 10 which is now enriched with polyamine or, in the case of a (partly) disconnected method of procedure, isolation of the mixture of organic phases 8 $b$ and 10 may be carried out by the usual method of distillation in apparatus F, optionally after rendering the phases alkaline with sodium hydroxide solution. The products obtained at this stage consist of hydrophobic solvent 8 $a$ which contains a maximum of 10% by weight of aniline, aniline 4 and 7 and polyamine mixture 11. The fact that the solvent 8 *a* may contain up to 10% of aniline substantially relieves the load on the distillation apparatus F.

This polyamine mixture 11 dissolved in an inert solvent such as chlorobenzene is reacted with phosgene in an apparatus in the usual manner to produce a polyisocyanate mixture 12 which is conveyed to the distillation stage H in which separation into a mixture of diisocyanate isomers 13 and a sump 14 which contains polyisocyanates takes place. In order that high yields may be obtained, this distillation, as well as subsequent distillations, must be carried out in an efficient vacuum, generally better than 10 Torr. Evaporators which are particularly suitable for this purpose are apparatus which have a large heating surface with a small liquid content, such as falling film evaporators equipped with circulating pumps to force circulation or thin layer evaporators with rigid rotors or with movable wiper blades.

To improve the purity of the distillate, distillation at the stage H may also be carried out over a column, preferably high-vacuum trickle film columns which operate at low pressure losses and are equipped with wire spirals (system Montz) or fabric packings (system Sulzer or system Montz) as exchange surfaces.

Separation of isomeric diphenylmethane diisocyanates takes place in the following distillation stage I, e.g. using one or more high-vacuum trickle film columns which may be arranged in series. These columns also require the use of evaporators which operate at low pressure losses and with small liquid contents. The distillate obtained is an isomeric mixture 15 enriched in 2,4'-diisocyanato-diphenylmethane. When suitably designed, these columns may also be used for preparing pure 2,4'-diisocyanato-diphenylmethane with a low isomer content of less than 3%.

The final distillation of the sump product 16 is carried out in the distillation stage A which, basically, is equipped in the same way as the distillation stage H, i.e. with an evaporator operating at low pressure loss and, optionally, using a high-vacuum trickle film column.

The distillate obtained is 4,4'-diisocyanato-diphenylmethane 17. The sump 18 may be returned to the distillation stage H 18 *a* or removed as another end product 18 *b*.

FIG. 2 shows a particular embodiment of the apparatus represented in FIG. 1.

In FIG. 2, the references A–F and 5a and 5b have the same meanings as in FIG. 1. The additional extractor C1 shown in FIG. 2 serves to remove ammonium salts carried into the organic solution leaving extractor C by washing the solution with water which has been obtained by distillation from the reactor B or from the evaporator E 5c. The aqueous phase 5d leaving the extractor C1 is returned to the beginning of the process. Excess water 5 is taken off the system.

The products of the process are valuable raw materials for the production of polyurethane plastics. Diphenylmethane-4,4'-diisocyanate, in particular, is a well known starting material for elastomers, fibers, thermoplastic resins and coatings, synthetic leather and tough elastic foam resins.

The invention is further illustrated by the following examples in which all parts and percentages are by weight unless otherwise specified.

EXAMPLE 1

In a continuously running cyclic systems arylamine mixture 1 and 30% aqueous formaldehyde solution 2 are continuously fed from a mixing nozzle into a cascade of 6 stirrer vessels. Streams 1 which consists of stream 9 plus additional HCl (not shown in the drawing) and 2 have the following composition in kg per hour:

1.
650 aniline
60 polyamine mixture
2 methanol
80 xylene
263 hydrogen chloride
947 water 2.
46 formaldehyde
2 methanol
105 water The temperature of the reaction mixture rises from 35°C in the first reactor to 102°C in the last reactor through an intermediate stage of 55°C. The first two reactors must be cooled and the subsequent reactors must be heated. A further 282 kg per hour of fresh aniline 3 and 340 kg per hour of recovered aniline 4 are added to the reaction mixture before it is introduced into the third reactor. 134 kg per hour of water contaminated with methanol, xylene and aniline 5 *a* are distilled from the sixth reactor.

The hot reaction mixture 6 enters an extraction system C consisting of three mixer/separator batteries arranged behind one another and a first sieve bottom column, and from there it enters a second sieve bottom column D. 2407 kg per hour of aniline 7 obtained from a plant for the recovery of aniline and xylene and the organic phase from the second extraction column D are introduced as extracting agent into the first extraction column. The extracting agent used for the second extraction column D is 2507 kg per hour of xylene 8. When the extracted aqueous phase 9 is represented with 30 kg per hour of 30% hydrochloric acid, it is the same as the stream 1. This means that from the total amount of 263 kg per hour of hydrogen chloride which is present in the initial stream 1 and which is sufficient to protonize at least 90% of the amino groups present in stream 1 only 9 kg per hour are lost and must therefore be replaced.

The organic phase 10 leaving the extraction system C is first made alkaline with 27 kg per hour of 50% sodium hydroxide solution, and, after separation of an aqueous phase it is transferred to a multi-stage vacuum distillation apparatus F. In this apparatus, fractional distillation results in a stream 8 of 2507 kg per hour of xylene with a residual aniline content of 7 kg per hour, streams 4 and 7 of 2747 kg per hour of aniline, and 300 kg per hour of polyamine mixture 11. The polyamine mixture prepared in this way contains 95.5% of diphenylmethane diamines with a diphenylmethane-2,4'-diamine content of 4.8%.

Reaction of the polyamine mixture with phosgene in a commercial plant G, using the chlorobenzene as solvent, results in a polyisocyanate mixture which after removal of the solvent is used as starting material 12 for the multi-stage distillation H, J and K.

This product 12 supplied at the rate of 375 kg per hour is mixed with 15 kg per hour of sump product 18 *a* from the last distillation stage K before entering the first distillation stage H.

The first distillation stage consists of a circulating evaporator followed by a drip separator, condensers and pumps. Distillation is carried out under a vacuum of 3 Torr at a sump temperature of 215°C. 315 kg per hour of distillation 13 and 63 kg per hour of a sump product 14 which has a viscosity of 240 cP at 25°C are obtained. Distillate 13 enters distillation stage J which is a series of two columns the first of which is packed with Sulzer BX type wire mesh, and from the sump of this first column it enters the second column which is packed with Sulzer BX type wire mesh and in which there is a head vacuum of 2 Torr and a sump temperature of 210°C. 3 kg per hour of distillate are removed from the first column and mixed with the sump product 14 (not shown in the drawing) to form a product which has a viscosity of 195 cP/25°C. The distillate 15 removed from the second column at the rate of 19 kg per hour at 2 Torr/170°C at the head of the column contains 60% of diphenylmethane-2,4'-diisocyanate.

The sump product 16 which is obtained from the second column(JII) at the rate of 311 kg per hour is distilled in a final column K packed with system Montz spiral springs at a head pressure of 2 Torr and a sump temperature of 210°C, being thereby separated into diphenylmethane-4,4'-diisocyanate 17 which is produced at the rate of 293 kg per hour and contains 0.9% of diphenylmethane-2,4'-diisocyanate, and a sump product 18 a obtained at the rate of 15 kg per hour. The sump product is returned to the stream 12.

EXAMPLE 2

120 parts of a polyisocyanate mixture 12 prepared according to the process described in Example 1 and consisting of 90% of diisocyanate with a diphenylmethane-2,4'-diisocyanate content of 4.55 and 10% of polyisocyanates which have a functionality greater than 2 are introduced into distillation stage H which is operated at a head pressure of up to 3 Torr, 35 parts of the polyisocyanate mixture being obtained as sump product and 85 parts of diisocyanate being removed as head product. Distillation is carried out with 22 parts of return flow. The distillate from the distillation stage H is supplied to the two high vacuum trickle film columns J which are connected in parallel and operated at 1.5 Torr and in which the lower boiling diphenylmethane-2,4'-diisocyanate is separated from the corresponding 4,4'-isomer 16. In each of these columns, 3 parts are removed as head product 15 and 67 parts are transferred as return flow to the columns. The sump product 16 is fed into the final distillation apparatus K which consists of a high-vacuum trickle film column operated at a head pressure of up to 3 Torr. The distillate obtained consists of 71 parts, based on the 120 parts mentioned above, of diphenylmethane-4,4'-diisocyanate with a diphenylmethane-2,4'-diisocyanate content of 0.9%. 8 parts of the sump of column K are returned to the distillation stage H 18a. The return flow returned to the head of the column amounts to 58 parts.

EXAMPLE 3

120 parts of a polyisocyanate mixture 12 prepared according to Example 1 and consisting of 99% of diisocyanate with a diphenylmethane-2,4'-diisocyanate content of 9% and 1% of polyisocyanate are freed from polyisocyanate in the highvacuum trickling film column used as the distillation stage H as described above. 97 parts of diisocyanate 13 are distilled over the top and 4 parts of polyisocyante 14 are removed as sump phase. The diisocyanate is fed into a high-vacuum trickling film column J where 7 parts of head product with a diphenylmethane-2,4'-diisocyanate content of 72% are removed and the return flow is 87 parts.

The sump product 16 is separated in the final distillation stage K into 83 parts, based on the 120 parts originally put into the reaction, of diphenylmethane-4,4'-diisocyanate with a diphenylmethane-2,4'-diisocyanate content of 0.8%, and 6 parts of sump product 18b.

EXAMPLE 4

120 parts of the polyisocyanate mixture defined in Example 3 are fed into two high-vacuum trickling film columns connected in series after passing through distillation stage H. In the first column of the distillation stage JI, operated at a head pressure of 1.5 Torr, 2 parts of first runnings are removed and returned to apparatus C. The sump product from the first column of stage J is fed into the second column of the distillation stage J where 6 parts of head product containing 71% of diphenylmethane-2,4'-diisocyanate are removed while the return flow is 87 parts. In distillation stage K, the sump product is separated as described above into 82 parts of diphenylmethane-4,4'-diisocyanate which a diphenylmethane-2,4'-diisocyanate content of 0.9% and 6 parts of sump product 18b.

Although the invention has been described in detail in the foregoing for the purposes of illustration, it is to be understood that such detail is solely for that purpose and that variations can be made therein by those skilled in the art without departing from the spirit and scope of the invention except as it may be limited by the claims.

What is claimed is:

1. A process for the simultaneous production of diisocyanates and higher functional polyisocyanates of the diphenylmethane series by reacting an arylamine which is at least partly protonized with formaldehyde in the aqueous phase, separating the resulting aniline/formaldehyde condensate from the resulting reaction product, phosgenating the separated aniline/formaldehyde condensate and working up the resulting polyisocyanate mixture by distillation; the said at least partly protonized arylamine being a mixture of
   a. aniline and
   b. a polyamine of the diphenylmethane series which has been obtained by aniline/formaldehyde condensation, the proportions of (a) to (b) corresponding to a ratio of aniline amino groups to polyamine amino groups of between 98:2 and 20:80, at least 90% of the amino groups in the mixture being protonized;

the aniline/formaldehyde molar ratio at the beginning of the reaction being between 1:1 and 12:1;

the condensation reaction being carried out in at least two stages, the reaction temperature in the first stage being 20° to 60°C and the reaction temperature in the last stage of condensation being above 60°C;

the separation of the polyamine which is to be phosgenated being carried out by
   a. extraction in at least two stages of the resulting reaction mixture with a hydrophobic solvent in the presence of additional aniline added to the condensation product in the aqueous phase during or before the condensation reaction and
   b. removal of water, hydrophobic solvent and aniline from the resulting organic phase being by distillation,
      a a. extraction being carried out at temperatures above 60°C in all stages of extraction,
      a b. the mixture conveyed to the first extraction stage for extraction containing 10 to 60 percent by weight of free arylamine,
a c. the hydrophobic solvent supplied to the first extraction stage containing 10 to 80 percent by weight of free aniline, and
a d. the hydrophobic solvent supplied to the last extraction stage containing a maximum of 10 percent by weight of free aniline, and
the aqueous phase obtained from the extraction process being returned to the beginning of the process.

2. The process of claim 1 wherein minor quantities of acid present in the form of ammonium salts are removed by washing with water or by neutralizing them with an aqueous inorganic base before the distillation (b).